ID=592 (no date).*

United States Patent
Sreeram et al.

(10) Patent No.: US 7,247,291 B2
(45) Date of Patent: Jul. 24, 2007

(54) NANO SIZED SULFIDE COMPOUNDS OF CERIUM AND A PROCESS FOR THE PREPARATION THEREOF

(76) Inventors: Kalarical Janardhanan Sreeram, c/o Central Leather Research Institute, Adyar, Chennai-600 020, Tamilnadu (IN); Harinarain Yamini Shrivastava, c/o Central Leather Research Institute, Adyar, Chennai-600 020, Tamilnadu (IN); Balachandran Unni Nair, c/o Central Leather Research Institute, Adyar, Chennai-600 020, Tamilnadu (IN); Thirumalachari Ramasami, c/o Cental Leather Research Institute, Adyar, Chennai-600 020, Tamilnadu (IN); Upadhyayula Venkata Varadaraju, c/o Indian Institute of Technology, Chennai-600 036, Tamilnadu (IN)

( * ) Notice: Subject to any disclaimer, the term of this patent is extended or adjusted under 35 U.S.C. 154(b) by 0 days.

(21) Appl. No.: 11/365,763

(22) Filed: Mar. 1, 2006

(65) Prior Publication Data

US 2007/0131143 A1    Jun. 14, 2007

(30) Foreign Application Priority Data

Dec. 9, 2005    (IN) ........................ 3333/Del/2005

(51) Int. Cl.
*C01F 17/00* (2006.01)
*C04B 14/36* (2006.01)

(52) U.S. Cl. ................ 423/561.1; 106/401; 423/21.1; 423/565

(58) Field of Classification Search ............... 106/401; 423/21.1, 561.1, 565
See application file for complete search history.

(56) References Cited

U.S. PATENT DOCUMENTS

| 5,348,581 | A | * | 9/1994 | Chopin et al. ............... 106/461 |
| 5,401,309 | A | * | 3/1995 | Chopin et al. ............... 106/461 |
| 5,501,733 | A | * | 3/1996 | Macaudiere et al. ........ 106/461 |
| 5,968,247 | A | * | 10/1999 | Macaudiere ................. 106/401 |
| 6,203,768 | B1 | * | 3/2001 | McCormick et al. .......... 423/1 |
| 6,221,473 | B1 | * | 4/2001 | Aubert et al. ............... 428/221 |

OTHER PUBLICATIONS

Cerium—Cerium (Ce) Properties and Applications, http://www.azom.com/details.asp?ArticleID=592 (no date).*

* cited by examiner

*Primary Examiner*—Anthony J. Green
(74) *Attorney, Agent, or Firm*—Ladas and Parry LLP

(57) ABSTRACT

The present invention relates to nano sized sulfide compounds of cerium and a process for the preparation thereof. More particularly, the present invention provides novel nano sized particles of cerium sulfide as well as a novel process for the preparation of nano sized sulfide compounds of cerium by the bioreduction of cerium sulfate or cerium acetate, without resorting to chemical methods. A bioprocess is disclosed to treat trivalent Cerium salt with sulfate-reducing bacteria (SRB) under controlled conditions to obtain a biomass, which is subjected to staggered heating upto a temperature of 600-1500° C. The sulfide of Cerium is finally separated for application in pigment industry.

13 Claims, No Drawings

NANO SIZED SULFIDE COMPOUNDS OF CERIUM AND A PROCESS FOR THE PREPARATION THEREOF

FIELD OF THE INVENTION

The present invention relates to nano sized sulfide compounds of cerium and a process for the preparation thereof. More particularly, the present invention provides novel nano sized particles of cerium sulfide as well as a novel process for the preparation of nano sized sulfide compounds of cerium by the bioreduction of cerium sulfate or cerium acetate, without resorting to chemical methods. The process offers an environmentally friendly bioprocess for preparation of the red pigment g-cerium(III) sulfide, which is envisaged to have enormous potential application in paint industry.

DESCRIPTION OF THE PRIOR ART

Several pigments conventionally used in the paint industry are toxic. These include the barium chromates, the cadmium sulfides, lead anitmonate etc. Regulations in Europe concerning the protection of the environment have forced the paint industry to invest heavily in research programs on development of inorganic paints that are free of heavy metals such as lead, mercury, cadmium, antimony, arsenic, chromium, selenium etc. A range of color ranging from Bordeaux red to orange based on cerium sesquisulfide (g-$Ce_2S_3$) have been developed Chopin et al. (U.S. Pat. No. 5401309, 1995) developed compounds of the type $M_2S_3$, where M is any element with atomic number between 57 to 71, by a thermodyanamically feasible process, whereby carbon-disulfide was used to enable the reaction to be carried out at temperatures as low as 1000° C. Aubert et al., (U.S. Pat. No. 6,221,472, 2001) have reported that the preparation methodology of the sulfide of a rare earth compound involves reacting a rare earth carbonate or hydroxycarbonate with hydrogen sulfide or carbon disulfide. Macaudiere et al., (U.S. Pat. No. 5,501,733, 1996) and Chopin et al., (U.S. Pat. No. 5,401,309, 1995) have reported that the cerium sesquisulfie generated can be fluorinated or doped with alkali or alkaline earth metals to generate a range of doped sulfides of cerium exhibiting varying shades. It is possible to vary the shade from Bordeaux red to orange by varying the oxygen content of the resultant cerium sulfide.

A closer analysis of the patented literature as mentioned above on the preparation of cerium sulfide would indicate the use of a hydrogen sulfide or carbon disulfide or mixture of the above at temperature conditions varying from 650-1300° C. The major limitation of using hydrogen sulfide for the preparation of the sulfides of cerium is that the process is environmentally insecure and constrained. The increasing global consciousness about the environmental hazards has prompted the researchers to look for better eco-benign options for preparing the metal sulfides. As reported by Klaus-Joerger et al., (Trends in Biotechnology, vol 19, 15, 2001) chemical processes need to be replaced by biological processes and towards this the use of sulfate reducing bacteria offer wide opportunities.

Metal-microbe interactions have an important role in several biotecnological applications, including the fields of biomineralization, bioremediation, bioleaching and microbial corrosion, and have gained growing attention in recent years. For example, the understanding of microbial-influenced corrosion processes in terms of localized changes in the surface chemistry of carbon steel or other alloys has improved. Bacteria also intervene in mineral precipitation reactions directly as catalysts of aqueous chemical reactions and indirectly as geochemically reactive solids. The bacterial oxidation of minerals is important in the formation of acid mine drainage and the extraction of gold, copper and uranium from ores. Klaus-Joerger et al., (Trends in Biotechnology, vol 19, 15, 2001) have reported commercially exploited processes based on bacterial oxidation. Moosa et al., (Chemical Engineering Science, vol. 57, p.2773, 2002) have reported biological methods for the reduction of sulfate in contaminated waters. In these processes, hydrogen sulfide produced by the Sulfate-reducing bacteria (SRB) is used to precipitate metal sulfides. Sulfate-reducing bacteria couple the oxidation of organic compounds or molecular $H_2$ with the reduction of sulfate as an external electron acceptor under anaerobic conditions, a process known as dissimilatory sulfate reduction. According to White et al., (FEMS Microbiological Reviews, vol 20, p.503, 1997) the end product of this reaction, hydrogen sulfide can react with heavy-metal ions to form insoluble metal sulfides or reduce soluble toxic metals, often to less toxic or less soluble forms.

The use of sulfate reducing bacteria for the removal of copper, chromium and other metal ions (like Fe, Zn, Pb and Cd) commonly found in acid mine drainage has been reported by Kauffman et al. (U.S. Pat. No. 4522723, 1985) and Gracia et al., (Minerals Engineering, Vol. 14, p.997, 2001). The process pertains essentially to a two-step mechanism for bacterially facilitated mineral formation, whereby in the first step, the metal ion binds to an active site on the cell wall and in the second step, this metal ion acts as a nucleation site for further metal deposition either as hydroxide or sulfide or both. Jalali et al., (Water Research, Vol. 34, p.797, 2000) report that the cell wall serves as a nucleation site for the metal deposition and subsequent mineralization. The major limitation associated with these methods is that they result in the formation of the metal hydroxide during the formation of metal sulfide.

The sulfate reducing bacteria employed in these efforts fall under the genera *Desulfovibrio* and *Desulfatomaculum* commonly found in wetlands, marine sediments and acid mine drains. Lens et al., (Critical Reviews in Environmental Science and Technology, Vol. 28, p.41, 1998) report that these bacteria are known to have a high demand for iron and have an optimum activity at pH of 7.3 to 7.6. The presence of high concentrations of hydrogen sulfide generated from the sulfate reduction process has been reported to be toxic to the sulfate reducing bacteria by Lens et al. (Critical Reviews in Environmental Science and Technology, Vol. 28, p.41, 1998). Moosa et al., (Chemical Engineering Science, vol. 57, p.2773, 2002) report that metallic micronutrients like cobalt, manganese, nickel etc were found to be essential for the optimal growth of the bacteria. The conditions optimal for the growth of the sulfate reducing bacteria are an anaerobic environment, a redox potential of below −100 mV and a pH higher than 5.5. According to White et al., (FEMS Microbiological Reviews, vol 20, p.503, 1997), while the main mechanism of removal of metal ions from solution by SRB's are that of formation of metal sulfides, the solubility of most toxic metal compounds, is also lower at neutral pH. In addition to lowering the solubility of metal sulfides, an elevation in pH can also contribute directly to precipitation of certain metals. Cerium compounds for instance are known to form hydroxides at pH above 5.5.

To date there are no reports for preparation of cerium sulfide—an environmentally friendly alternative to red colored cadmium sulfide pigment, by methods other than that using toxic chemicals like hydrogen sulfide and carbon disulfide. Further, a biological route to the preparation of cerium sulfide using sulfate reducing bacteria would involve a pH of above 6.0, wherein cerium hydroxide would be coprecipiated along with cerium sulfide, resulting in a impure composition which will not find applications as a red pigment. This necessitates the development of nano sized cerium(III) sulfides from cerium(III) sulfates by bioreduction by employing sulfate reducing bacteria at pH conditions below 6, wherein cerium hydroxide is not coprecipitated.

OBJECTS OF THE INVENTION

The main objective of the present invention is to provide a novel bioprocess for preparation of sulfide compounds of cerium, which precludes the drawbacks stated above.

Another objective of the present invention is to use Sulfate-reducing bacteria having the following characteristics. a) They can grow using countless organic compounds as sources of energy for their metabolism and most of the species can oxidize these compounds completely to $CO_2$, b) They can convert sulfate to sulfide, c) They can utilize sulfate ion as an electron acceptor during the oxidation of organic material, forming hydrogen sulfide that forms insoluble complexes with many heavy metals. The growth of sulfate reducing bacteria are detected by the formation of black precipitates in the presence of Postgate's C medium comprising of 0.5 g/L dihydorgen potassium phosphate, 1.0 g/L of ammonium chloride, 0.06 g/L of magnesium sulfate heptahydrate, 3.5 g/L of sodium lactate (70%), 1.0 g/L of yeast extract, 1.0 g/L of calcium sulfate, 0.01 g/L of ferrous sulfate heptahydrate, 4.5 g/L of sodium sulfate, 0.06 g/L of calcium chloride hexahydrate, 0.3 g/L of sodium citrate, with pH adjusted to 7.0 with 10% w/v of sodium hydroxide.

Still another objective of the present invention is to provide for an environmentally safer biological route whereby the use of chemical methods using harmful compounds like hydrogen sulfide is avoided.

Yet another objective of the present invention is to bring about the reduction of cerium(III)sulfate to cerium(III)sulfide by the use of either known or mixed cultures of sulfate reducing bacteria.

Still another objective of the present invention is to acclimatize the sulfate reducing bacteria to grow at pH conditions of 2-6 and cerium concentration of 1000 mg/lit, there by providing for a single step process for preparation of sulfide compounds of cerium, without the formation of cerium hydroxide.

Yet another objective of the present invention is to provide for a nano sized sulfide compound of cerium which can either be used as a pigment or a precursor for the preparation of red pigment—g-Cerium sulfide.

SUMMARY OF THE INVENTION

Accordingly, the present invention provides a novel bioprocess for the preparation of sulfide compounds of cerium, which comprises:
i) treating trivalent Cerium salt, optionally in combination with 0.005-0.1% w/v, of sodium sulfate, with a culture broth of sulfate-reducing bacteria (SRB), exhibiting the characteristics as herein described and prepared by known methods, containing 0.05-1% v/v, of chloroform, under an inert atmosphere, at a temperature ranging between 25-40° C., at pH of 2 to 6 for a period in the range of 3 to 45 days in single or several installments such that the trivalent Cerium ion concentration does not exceed beyond 0.1% w/v at any point of time to obtain a biomass,
ii) concentrating the biomass as obtained in step(i), by known methods at a temperature ranging between 60 to 150° C. for a period in the range of 1 to 6 hours to get the concentrated biomass,
(iii) treating the concentrated biomass as obtained in step(ii) at a temperature between 600 to 1500° C. for a period in the range of 5 to 400 minutes followed by separation by known method to obtain sulfide of Cerium.

In an embodiment of the present invention, the trivalent cerium salt used may be selected from cerium(III)sulfate, cerium(III)acetate either alone or in any combination.

In another embodiment of the present invention, the sulfate-reducing bacteria used may be selected from *Desulfovibrio desulfuricans* (ATCC 29577), *Desulfovibrio devulgaris* (ATCC 29579), mixed populations of naturally occurring sulfate reducing bacteria, collected from natural sources, as herein described.

In yet another embodiment of the present invention, the natural source for collecting mixed populations of naturally occurring sulfate reducing bacteria may be such as, but not limited to tannery wastewaters, wetlands or marine sediments, acid mine drains, household sewage and swamps.

In still another embodiment of the present invention, the condition for growing the SRB culture is anaerobic.

In yet another embodiment of the present invention, the culture broth may be prepared using 0.05-2% w/v, of peptone with a known energy source.

In still another embodiment of the present invention, the energy source for growing the SRB culture may be such as 0.5-3% w/v, of organic carbon, 0.1-10% v/v of hydrogen, either individually or in any combination.

In yet another embodiment of the present invention, the source for the organic carbon may be such as, but not limited to acetate, lactate, ethanol, methanol, glycerol, glucose, yeast extract, beef extract and molasses, either individually or in any combination.

In still another embodiment of the present invention, pH of the culture medium for growing the SRB culture may be in the range of 2-6.

In yet another embodiment of the present invention, the cell count of the SRB may be in the range of $10^6$ to $10^9$ cells/ml In still another embodiment of the present invention, the known method for concentration of the biomass may be such as evaporation, centrifugation.

In yet another embodiment of the present invention, the sulfide of cerium prepared may be such as cerium sulfide (CeS), cerium oxysulfide, g-cerium sulfide.

In still another embodiment of the present invention, the particle size of the sulfide compound of cerium may be in the range of 15-100 nanometers.

DETAILED DESCRIPTION OF THE INVENTION

The process of the present invention is described below in detail.

The sulfate reducing bacteria (SRB) culture broth is prepared by the following known method. The SRB sourced from designated isolate or natural sources such as tannery wastewaters, natural swamps, marshy land, acid mine drains etc. is grown on prepouredculture plates comprising of a nutrient agar media and incubated overnight at 37° C. On the next day, after monitoring the positive growth of the bacteria, single colonies are subcultured further to obtain purer cultures. The cultures are then transferred to a broth consisting of peptone. On the next day, after monitoring the positive growth of the bacteria, single colonies are subcultured further to obtain purer cultures. The cultures are then transferred to a broth consisting of 0.05-2% w/v, of peptone and 0.5-3% w/v, of an organic carbon source or 0.1-10 v/v hydrogen gas (purged slowly and intermittently during the reduction process). pH of the culture medium is maintained in the range of 2-6. The bacteria are acclimatized to grow at the desired pH by a slow gradation process so that Cerium hydroxide is not coprecipitated along with the generated sulfide compounds of Cerium. Strict anaerobic conditions are established by storing the broth in airtight containers and evacuating any gas in the container, by purging with an inert gas like nitrogen or argon. 0.5-1.0% v/v of Chloroform is added to the broth to ensure the removal of methanogenic bacteria.

A trivalent Cerium salt optionally in combination with 50-1000 mg/L of sodium sulfate is introduced in the SRB broth either intermittently or in one shot. The cell count of the SRB is maintained at a range of $10^6$ to $10^9$ cells/ml. It is ensured that the proportion of the trivalent Cerium ion does not exceed 1000 mg/lit at any point of time. The reaction is allowed to continue at a temperature ranging between 25-45° C. for a period in the range of 3 to 45 days under an inert atmosphere. The resulting biomass is concentrated by known method at a temperature ranging between 60-150° C. for a period of 1-6 hours. The concentrated biomass is then heated in inert atmosphere, at a temperature between 600-1500° C. for a time period of 5-400 mins followed by separation by known method to obtain sulfides of cerium The inventive step of the present invention lies in the single step treatment of trivalent salt of cerium, which need not necessarily be a sulfate, with sulfate reducing bacteria under controlled conditions to prepare sulfide of Cerium without generating cerium hydroxide or any other byproduct, that may adversely affect either the crystalline purity or color of Cerium sulfide for use in paint industry or does not use such chemicals which are harmful to the environment.

The invention is described in detail in the following examples, which are provided by way of illustration only and therefore should not be construed to limit the scope of the present invention.

EXAMPLE 1

A nutrient agar media was prepared by adding 2.5 g of peptone, 0.75 g of yeast, 0.75 g of beef extract, 2.5 g of sodium chloride, 10 g of agar in 500 ml of water and adjusting the pH to 7.0. The media was autoclaved at 15 lbs pressure for 15 min., then poured on to previously sterilized glass plates and allowed to solidify. By employing the quadrant streaking method, 1 mL of tannery wastewater was streaked on to the nutrient agar plate. The plates were incubated overnight at 37° C. The next day the growth of the bacteria was monitored and a single colony was streaked onto a fresh nutrient agar plate maintained at pH 6.0. The subculturing was repeated three times and the culture thus obtained was used for the reduction studies. An acetate media consisting of 0.5 g of peptone and 10.0 g of sodium acetate in 500 ml of water was prepared, autoclaved, cooled and transferred to an air tight glass reactor. Oxygen, if any, present in the reactor was removed by purging with an inert gas (nitrogen). A loop of the bacterial culture from the agar plate was added and the broth kept stirring. 2.5 ml of chloroform was added to the broth. 250 mg of Cerium(III) sulfate was added to the reactor. Nitrogen gas was purged into the reactor intermittently to remove any gas generated during the reaction. After 20 days, a complete reduction of cerium(III) sulfate was observed. The biomass was concentrated in a rotary evaporator at 60° C. for one hour and then treated in nitrogen atmosphere at 925° C. for 60 minutes to obtain cerium(III) sulfide. The X-ray diffraction indicated the sulfide compound to be cerium oxysulfide. Particle size measurement of pigment indicated the size to be 23±3 nm. The cerium oxysulfide prepared was stable at room temperature and had a shelf life of above 3 months.

EXAMPLE 2

A nutrient agar media was prepared by adding 2.5 g of peptone, 0.75 g of yeast, 0.75 g of beef extract, 2.5 g of sodium chloride, 10 g of agar in 500 ml of water and adjusting the pH to 7.0. The media was autoclaved at 15 lbs pressure for 15 min., then poured on to previously sterilized glass plates and allowed to solidify. By employing the quadrant streaking method, 1 ml of wet soil from a marshy land was streaked on to the nutrient agar plate. The plates were incubated overnight at 37° C. The next day the growth of the bacteria was monitored and a single colony was streaked onto a fresh nutrient agar plate, maintained at pH 6.0. The subculturing was repeated at pH 5.0 and the culture thus obtained was used for the reduction studies. An acetate media consisting of 1.0 g of peptone and 5.0 g of sodium acetate in 500 ml of water was prepared, autoclaved, cooled and transferred to an air tight glass reactor. Oxygen, if any, present in the reactor was removed by purging with an inert gas (nitrogen). A loop of the bacterial culture from the agar plate was added and the broth kept stirring. 3 ml of chloroform was added to the broth. 300 mg of Cerium(III) sulfate was added to the reactor. Nitrogen gas was purged into the rector intermittently to remove any gas generated during the reaction. After 20 days, a complete reduction of cerium(III) sulfate was observed. The biomass was concentrated in a rotary evaporator at 90° C. for 2 hrs and then treated in nitrogen atmosphere at 925° C. for 45 minutes to obtain cerium(III) sulfide. The X-ray diffraction indicated the sulfide compound to be cerium oxysulfide. Particle size measurement of pigment indicated the size to be 60±5 nm. The cerium oxysulfide prepared was stable at room temperature and had a shelf life of above 3 months. The product had very good phase purity and outstanding increased chromatic coordinates in the specific color.

EXAMPLE 3

A nutrient agar media was prepared by adding 2.5 g of peptone, 0.75 g of yeast, 0.75 g of beef extract, 2.5 g of sodium chloride, 10 g of agar in 500 ml of water and adjusting the pH to 7.0. The media was autoclaved at 15 lbs pressure for 15 min., then poured on to previously sterilized glass plates and allowed to solidify. By employing the quadrant streaking method, 1 ml of acid mine drain wastewater was streaked on to the nutrient agar plate. The plates were incubated overnight at 37° C. The next day the growth of the bacteria was monitored and a single colony was streaked onto a fresh nutrient agar plate, maintained at pH 6.0. The subculturing was repeated and the culture thus obtained was used for the reduction studies. A lactate media consisting of 1.0 g of peptone and 40 ml of 40% lactic acid in 500 ml of water was prepared, autoclaved, cooled and transferred to an airtight glass reactor. Oxygen, if any, present in the reactor was removed by purging with an inert gas (argon). A loop of the bacterial culture from the agar plate was added and the broth kept stirring. 5 ml of chloroform was added. 500 mg of Cerium(III) sulfate was added to the reactor intermittently (with 100 mg every 5 days). Nitrogen gas was purged into the reactor intermittently to remove any gas generated during the reaction. After 30 days, a 95% reduction of cerium(III) sulfate was observed. The biomass was concentrated in a rotary evaporator at 70° C. for one hour and the same treated in nitrogen atmosphere at 1300° C. for one hour to obtain cerium(III) sulfide. The X-ray diffraction indicted the sulfide compound to be a mixture cerium oxysulfide and cerium sulfide.

EXAMPLE 4

A nutrient agar media was prepared by adding 2.5 g of peptone, 0.75 g of yeast, 0.75 g of beef extract, 2.5 g of sodium chloride, 10 g of agar in 500 ml of water and adjusting the pH to 7.0. The media was autoclaved at 15 lbs pressure for 15 min., then poured on to previously sterilized glass plates and allowed to solidify. By employing the quadrant streaking method, 1 ml of slurry from a swamp was streaked on to the nutrient agar plate. The plates were incubated overnight at 37° C. The next day the growth of the bacteria was monitored and a single colony was streaked onto a fresh nutrient agar plate, maintained at pH 7.0. The subculturing was repeated at pH 5.0, 4.0 and then at pH 2.0 and the culture thus obtained was used for the reduction studies. A media consisting of 1.0 g of peptone and 15 g of glucose in 500 ml of water was prepared, autoclaved, cooled and transferred to an air tight glass reactor. Oxygen, if any, present in the reactor was removed by purging with an inert gas (nitrogen). A loop of the bacterial culture from the agar plate was added and the broth kept stirring. 2.5 ml of chloroform was added to remove any methanogenic bacteria. 500 mg of Cerium(III) sulfate was added to the reactor intermittently (with 100 mg every 3 days). Argon gas was purged into the reactor intermittently to remove any gas generated during the reaction. After 23 days, a 95% reduction of cerium(III) sulfate was observed. The biomass was concentrated in a centrifuge at 60° C. for one hour and the same treated in nitrogen atmosphere at 900° C. for two hours to obtain cerium(III) sulfide. The X-ray diffraction indicated the sulfide compound to be a g-cerium(III)sulfide. Particle size measurement of pigment indicated the size to be 31±3 nm. The cerium sulfide prepared was stable at room temperature and had a shelf life of above 3 months and had a bright red color. The product had very good phase purity and outstanding increased chromatic coordinates in the specific color.

EXAMPLE 5

An acetate media consisting of 1.0 g of peptone and 40 ml of 40% lactic acid in 500 ml of water was prepared, autoclaved, cooled and transferred to an air tight glass reactor. Oxygen, if any, present in the reactor was removed by purging with an inert gas (nitrogen). A loop of the *Desulfovibrio desulfuricans* from an already prepared agar plate was added and the broth kept stirring. 300 mg of Cerium(III) sulfate was added to the reactor intermittently (with 100 mg every 5 days). Nitrogen gas was purged into the reactor intermittently to remove any gas generated during the reaction. After 18 days, a 95% reduction of cerium(III) sulfate was observed. The biomass was concentrated in a rotary evaporator at 150° C. for one hour and then treated in nitrogen atmosphere at 1000° C. for thirty minutes to obtain cerium(III) sulfide. The X-ray diffraction indicated the sulfide compound to be a cerium sulfide (CeS). Particle size measurement of pigment indicated the size to be 90±6 nm. The cerium sulfide prepared was stable at room temperature and had a shelf life of above 3 months. The product had very good phase purity and outstanding increased chromatic coordinates in the specific color.

EXAMPLE 6

A media consisting of 1.0 g of peptone in 500 ml of water was prepared, autoclaved, cooled and transferred to an air tight glass reactor. Oxygen, if any, present in the reactor was removed by purging with an inert gas (nitrogen). A loop of the *Desulfovibrio devulgaris* from an already prepared agar plate was added and the broth kept stirring. Approximately 1 ml of Hydrogen gas was purged into the reactor every 3 hrs. 400 mg of Cerium(III) sulfate was added to the reactor intermittently (with 100 mg every 5 days). Nitrogen gas was purged into the reactor intermittently to remove any gas generated during the reaction. After 23 days, a complete reduction of cerium(III) sulfate was observed. The biomass was concentrated in a rotary evaporator at 100° C. for four hours and then treated in nitrogen atmosphere at 600° C. for thirty minutes to obtain cerium(III) sulfide. The X-ray diffraction indicated the sulfide compound to be a mixture cerium oxysulfide and cerium sulfide.

EXAMPLE 7

A media consisting of 1.0 g of peptone in 500 ml of water was prepared, autoclaved, cooled and transferred to an air tight glass reactor. Oxygen, if any, present in the reactor was removed by purging with an inert gas (nitrogen). A loop of the *Desulfovibrio devulgaris* from an already prepared agar plate was added and the broth (500 ml) kept stirring. Approximately 3 ml of Hydrogen gas was purged into the reactor every 3 hrs. 50 mg of Cerium(III) acetate and 33 mg of sodium sulfate was added to the reactor. Nitrogen gas was purged into the reactor intermittently to remove any gas generated during the reaction. After 3 days, a 90% reduction of sulfate ions was observed. The biomass was concentrated in a rotary evaporator at 80° C. for one hour and then treated in nitrogen atmosphere at 600° C. for thirty minutes to obtain cerium(III) sulfide. The X-ray diffraction indicated the sulfide compound to be cerium oxysulfide. Particle size measurement of pigment indicated the size to be 23±3 nm. The cerium oxysulfide prepared was stable at room temperature and had a shelf life of above 3 months. The product had very good phase purity and outstanding increased chromatic coordinates in the specific color.

EXAMPLE 8

A media consisting of 1.0 g of peptone and 4 g of molasses in 500 ml of water was prepared, autoclaved, cooled and transferred to an air tight glass reactor. Oxygen, if any, present in the reactor was removed by purging with an inert gas (nitrogen). A loop of the *Desulfovibrio devulgaris* from an already prepared agar plate was added and the broth kept stirring. Approximately 2 ml of Hydrogen gas was purged into the reactor every 3 hrs. 400 mg of Cerium (III) sulfate was added to the reactor intermittently (with 100 mg every 5 days). Nitrogen gas was purged into the reactor intermittently to remove any gas generated during the reaction. After 23 days, a complete reduction of cerium(III) sulfate was observed. The biomass was concentrated in a rotary evaporator at 100° C. for four hours and then treated in nitrogen atmosphere at 600° C. for thirty minutes to obtain cerium(III) sulfide. The X-ray diffraction indicted the sulfide compound to be a mixture cerium oxysulfide and cerium sulfide.

The following are the advantages of the present invention:
1. This process provides for a environmentally benign biomimetic route to the preparation of cerium(III) sulfide which finds use in pigments or as a precursor to pigments, as a replacement for the carcinogenic cadmium sulfide based pigments.
2. This process makes use of harmless microorganisms commonly found in wastewaters, swamps, marshy lands etc or isolated cultures of sulfate reducing bacteria.
3. The process of the present invention relates essentially to the bioreduction of cerium sulfate to cerium sulfide with the help of sulfate reducing bacteria. The process does not employ any chemical method that generates harmful gases like hydrogen sulfide. However, there is a possibility that the said bioreduction involves in situ generation of hydrogen sulfide which precipitates the cerium as cerium sulfide. But this generation, if any, is utilized by the reduction process immediately ensuring that no free hydrogen sulfide is released, till such time that cerium sulfate is present. Thus the process does not result in any environmental hazard. Further, the bioreduction process is very slow, whereby there is hardly any possibility of accumulation of any hydrogen sulfide in the system. This also derives ample support from a similar observation, as reported by Vainshtein et al., (Water Research, Vol. 37, 1401, 2003), in the context of conversion of hexavalent chromium to trivalent chromium.
4. In contrast to the prior art processes for the preparation of sulfides of rare earth compounds, which involve essentially three steps, as indicated below
    a. bringing into contact at least one rare earth carbonate or hyroxycarbonate with at least one compound of an alkali element
    b. heating said rare earth carbonate or hyroxycarbonate and the compound of an alkali element in the presence of hydrogen sulfide or carbon disulfide to obtain a rare earth sulfide
    c. reacting the rare earth sulfide obtained from b) with a fluorinating agent, the process of the present invention provides a single step process for generating sulfide compounds of cerium at pH of 2-6, by way of treating the cerium sulfate/acetate in a medium containing the sulfate reducing bacteria under controlled conditions, whereby the sulfate is reduced to sulfide—resulting in the formation of cerium sulfide, followed by concentration and burning off of the biomass to obtain crystalline pure g-cerium sulfide or a precursor to g-cerium sulfide. This single step bio-process, unlike the hitherto known multistep processes, while are essentially chemical based, does neither result in the concentration of other compounds of cerium like cerium hydroxide nor generates hazardous gases like hydrogen sulfide, while producing cerium sulfide.
5. The process of the present invention provides for the generation of cerium(III) sulfide particles of nano sizes.

We claim:
1. A bioprocess for the preparation of a sulfide compound of cerium, which comprises the steps of:
    a) treating trivalent Cerium salt, optionally in combination with 0.005-0.1% w/v, of sodium sulfate, with a culture broth of sulfate-reducing bacteria (SRB), containing 0.05-1% v/v, of chloroform, under an inert atmosphere, at a temperature ranging between 25-40° C., at pH of 2 to 6 for a period in the range of 3 to 45 days in single or several installments such that a concentration of trivalent Cerium ions does not exceed 0.1% w/v at any point of time, to obtain a biomass,
    b) concentrating the biomass as obtained in step a), at a temperature ranging between 60 to 150° C. for a period in the range of 1 to 6 hours to obtain a concentrated biomass, and
    c) treating the concentrated biomass as obtained in step b) at a temperature between 600 to 1500° C. for a period in the range of 5 to 400 minutes followed by separation to obtain a sulfide of Cerium.
2. A process as claimed in claim 1, wherein the trivalent Cerium salt used is selected from cerium(III)sulfate, cerium (III) acetate either alone or in any combination.
3. A process as claimed in claim 1, wherein the sulfate-reducing bacteria is selected from *Desulfovibrio desulfuricans* (ATCC 29577), *Desulfovibrio devulgaris* (ATCC 29579) or mixed populations of naturally occurring sulfate reducing bacteria collected from one or more natural sources.
4. A process as claimed in claim 3, wherein the natural sources for collecting mixed populations of naturally occurring sulfate reducing bacteria are tannery wastewaters, wetlands or marine sediments, acid mine drains, household sewage, and swamps.
5. A process as claimed in claim 1, wherein the sulfate reducing bacteria is grown under anaerobic conditions.
6. A process as claimed in claim 1, wherein the culture broth of sulfate reducing bacteria is prepared using 0.05-2% w/v of peptone with an energy source.
7. A process as claimed in claim 6, wherein the energy source for growing the sulfate reducing bacteria is 0.5-3% w/v of organic carbon, 0.1 to 10% v/v hydrogen, either individually or in any combination.
8. A process as claimed in claim 7, wherein the source of organic carbon is acetate, lactate, ethanol, methanol, glycerol, glucose, yeast extract, beef extract and molasses, either individually or in any combination.
9. A process as claimed in claim 1, wherein the culture medium is of a pH in the range of 2-6.
10. A process as claimed in claim 1, wherein the concentration of sulfate reducing bacteria is in the range of $10^6$ to $10^9$ cells/ml.
11. A process as claimed in claim 1, wherein the biomass is concentrated by evaporation, centrifugation or both.
12. A process as claimed in clima 1, wherein the sulfide of cerium prepared is cerium sulfide (CeS), cerium oxysulfide, or g-cerium sulfide.
13. A process as claimed in claim 1, wherein a size of cerium sulfide particles is in the range from 15-100 nanometers in size.

* * * * *